United States Patent [19]

Habicht et al.

[11] Patent Number: 4,517,184
[45] Date of Patent: * May 14, 1985

[54] BENZODIOXOLE DERIVATIVES

[75] Inventors: Ernst Habicht, Oberwil; Paul Zbinden, Witterswil, both of Switzerland

[73] Assignee: Ciba-Geigy Corporation, Ardsley, N.Y.

[*] Notice: The portion of the term of this patent subsequent to Nov. 8, 2000 has been disclaimed.

[21] Appl. No.: 521,483

[22] Filed: Aug. 8, 1983

Related U.S. Application Data

[63] Continuation-in-part of Ser. No. 369,873, Apr. 19, 1982, Pat. No. 4,414,214.

[30] Foreign Application Priority Data

Apr. 24, 1981 [CH] Switzerland ............... 2698/81

[51] Int. Cl.³ ............... A61K 31/455; C07D 407/06
[52] U.S. Cl. ............... 514/212; 260/244.4; 260/330.3; 260/330.9; 544/131; 544/146; 544/148; 549/60; 549/535; 549/536; 546/194; 546/197; 546/270; 548/526; 514/239; 514/338; 514/444; 514/465
[58] Field of Search ............... 260/330.3, 330.9, 244.4; 544/146, 148, 131; 546/197, 194, 270; 548/526; 549/60, 535, 536; 424/248.51, 248.57, 267, 274, 275, 282, 248.58, 263

[56] References Cited

U.S. PATENT DOCUMENTS

| | | | |
|---|---|---|---|
| 3,758,506 | 10/1973 | Jacques et al. | 424/275 X |
| 3,872,105 | 3/1975 | Grisar et al. | 424/282 X |
| 3,958,004 | 5/1976 | Cragoe et al. | 424/275 |
| 4,058,559 | 11/1977 | Jones et al. | 424/269 X |
| 4,156,011 | 5/1979 | Lafon et al. | 424/309 |
| 4,220,801 | 10/1980 | Walter et al. | 562/468 |
| 4,414,214 | 11/1983 | Habicht et al. | 424/248.51 |

OTHER PUBLICATIONS

Mastrocola et al., Chemical Abstracts, vol. 91, (1979) 193158t.

*Primary Examiner*—Richard L. Raymond
*Attorney, Agent, or Firm*—Irving N. Feit

[57] ABSTRACT

The invention relates to novel benzodioxole derivatives of the formula I

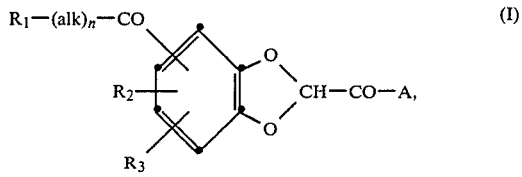

in which $R_1$ represents an unsubstituted or substituted, aromatic or heteroaromatic radical, alk represents an alkylene or alkylidene radical having a maximum of 5 carbon atoms, n represents 0 or 1, $R_2$ and $R_3$ each represents, independently of the other, hydrogen, lower alkyl, lower alkoxy or halogen, and A represents the radical $O-R_4$, wherein $R_4$ represents hydrogen or an unsubstituted or substituted, aliphatic or araliphatic hydrocarbon radical, or A represents the radical

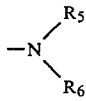

in which either $R_5$ and $R_6$ each represents, independently of the other, hydrogen or lower alkyl, or $R_5$ and $R_6$ are bonded to one another and, together with the adjacent nitrogen atom, represent unsubstituted or lower alkyl-substituted tetra- or hexa-methyleneimino or 4-morpholinyl, to salts of compounds of the formula I in which A represents $OR_4$ wherein $R_4$ is hydrogen, with bases, and to acid addition salts of compounds of the formula I in which the radical $R_1$ has a basic character, and to pharmaceutical compositions that contain them. The novel substances exhibit diuretic and, in addition, uricosuric activity and may be administered, according to the invention, preferably in the form of appropriate pharmaceutical compositions, to mammals for the treatment of oedema and hypertension.

5 Claims, No Drawings

BENZODIOXOLE DERIVATIVES

This application is a continuation-in-part of application Ser. No. 369,873 filed Apr. 19, 1982, U.S. Pat. No. 4,414,214.

The invention relates to novel benzodioxole derivatives with valuable pharmacological properties, to pharmaceutical compositions containing them, and to the use of these novel substances and pharmaceutical compositions.

The novel compounds according to the invention correspond to the formula I

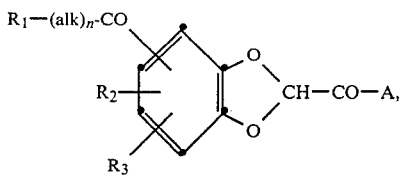

in which
- $R_1$ represents an unsubstituted or substituted, aromatic or heteroaromatic radical,
- alk represents an alkylene or alkylidene radical having a maximum of 5 carbon atoms,
- n represents 0 or 1,
- $R_2$ and $R_3$ each represents, independently of the other, hydrogen, lower alkyl, lower alkoxy or halogen, and
- A represents the radical —O—$R_4$, wherein $R_4$ represents hydrogen or an unsubstituted or substituted, aliphatic or araliphatic hydrocarbon radical, or A represents the radical

in which either $R_5$ and $R_6$ each represents, independently of the other, hydrogen or lower alkyl, or $R_5$ and $R_6$ are bonded to one another and, together with the adjacent nitrogen atom, represent unsubstituted or lower alkyl-substituted tetra- to hexamethyleneimino or 4-morpholinyl.

The novel compounds may be present in the form of racemates or optical antipodes or, with the appropriate meanings for the variables, alternatively in the form of a mixture of racemates. The invention relates also to salts of compounds of the general formula I in which A represents $OR_4$ wherein $R_4$ represents hydrogen, with bases, and to acid addition salts of compounds of the formula I in which the radical $R_1$ has a basic character. Unless otherwise stated, hereinbefore and hereinafter lower radicals or compounds are to be understood as those having a maximum of 7, preferably a maximum of 4, carbon atoms.

An aromatic radical $R_1$ is especially a 1- or 2-naphthyl radical and especially a phenyl radical. A heteroaromatic radical is preferably a bicyclic radical and especially a monocyclic radical. As a corresponding monocyclic radical, $R_1$ contains especially two nitrogen atoms or, preferably, one nitrogen atom and/or one oxygen or sulphur atom and is, for example, mono- or di-azacyclic, oxa- or thia-cyclic or oxaza- or thiazacyclic radical having 5 ring members, for example 1H-pyrrolyl, such as 1H-pyrrol-2-yl or -3-yl, 1H-pyrazolyl, such as 1H-pyrazol-3-yl, -4-yl or -5-yl, 1H-imidazolyl, such as 1H-imidazol-2-yl, -4-yl or -5-yl, furyl, such as 2- or 3-furyl, thienyl, such as 2- or 3-thienyl, oxazolyl, such as 2-oxazolyl, isoxazolyl, such as 3- or 5-isoxazolyl, thiazolyl, such as 2- or 4-thiazolyl, or a mono- or diazacyclic radical having 6 ring members, for example pyridyl, such as 2-, 3- or 4-pyridyl, pyridazinyl, such as 3-pyridazinyl, pyrimidinyl, such as 2-, 4- or 5-pyrimidinyl, or 2-pyrazinyl. Corresponding bicyclic radicals $R_1$ comprise, for example, a 5-membered hetero ring of aromatic character having two nitrogen atoms or having one nitrogen atom and/or one oxygen or sulphur atom as ring members and a fused-on benzene ring, or a 6-membered hetero ring of aromatic character having two or, especially, one nitrogen atom(s) as ring member(s) and a fused-on benzene ring. Accordingly, bicyclic heteroaryl is, for example, 1H-indolyl, such as 1H-indol-2-yl, -3-yl, -4-yl, -5-yl or -6-yl, 1H-indazolyl, such as 1H-indazol-3-yl, 1H-benzimidazolyl, such as 1H-benzimidazol-2-yl, -4-yl, -5-yl or -6-yl, benzofuranyl, such as 2-, 3-, 5- or 6-benzofuranyl, benzo[b]thienyl, such as benzo[b]thien-2-yl, -3-yl, -5-yl or -6-yl, benzoxazolyl, such as 2-, 4-, 5- or 6-benzoxazolyl, benzothiazolyl, such as 2-, 4-, 5- or 6-benzothiazolyl, or, for example, quinolinyl, such as 2-, 4-, 5- or 6-quinolinyl, isoquinolinyl, such as 1-, 3- or 4-isoquinolinyl, quinazolinyl, such as 2-, 4- or 6-quinazolinyl, quinoxalinyl, such as 2- or 6-quinoxalinyl, or phthalazinyl, such as 1- or 6-phthalazinyl. As a substituted aromatic or heteroaromatic radical, $R_1$ is substituted once or several times, preferably a maximum of three times, for example by halogen, such as fluorine, bromine, iodine or, especially, chlorine, by lower alkyl, such as, for example, ethyl, propyl, isopropyl, butyl, isobutyl, tert.-butyl or, especially, methyl, and/or by lower alkoxy, such as ethoxy, propoxy, isopropoxy, butoxy, isobutoxy and, especially, methoxy and/or by trifluoromethyl.

An alkylene or alkylidene radical alk may be straight-chain or branched and is, for example, 1,1- or 2,2- or 1,2-dimethylethylene, 1-ethylethylene, tetramethylene or 1-propylethylene or 1-methylpropylidene, 2-methylpropylidene, butylidene or 1-ethylpropylidene, but especially a radical containing a maximum of 3 carbon atoms, such as ethylene, propylene, trimethylene or ethylidene, propylidene, or 1-methylethylidene and, especially, methylene.

$R_2$ and $R_3$ are, as lower alkyl, for example ethyl, propyl, isopropyl, butyl, isobutyl or tert.-butyl and, especially, methyl; as lower alkoxy, for example ethoxy, propoxy, isopropoxy, butoxy, isobutoxy and, especially, methoxy, and as halogen, bromine, iodine, especially fluorine or, more especially, chlorine. In a radical A, $R_4$ as an unsubstituted or substituted, aliphatic or araliphatic hydrocarbon radical is, for example, alkyl having a maximum of 12 carbon atoms, especially lower alkyl, also 2- or 3-lower alkenyl, or 2-lower alkynyl, lower alkoxy-lower alkyl, halogenated lower alkyl, such as geminal polyhalo-lower alkyl, or, for example, phenyl-lower alkyl or cinnamyl in which the phenyl radical may be substituted, for example in the same manner as a phenyl radical $R_1$. Alkyl $R_4$ is, for example, propyl, isopropyl, butyl, isobutyl, pentyl, isopentyl, neopentyl, hexyl, heptyl, octyl, nonyl, decyl, dodecyl and, especially, methyl or ethyl; lower alkenyl $R_4$ is, for example, allyl, 1- or 2-methallyl, 2-butenyl or 3-butenyl; lower alkynyl is, for example, 2-propynyl; lower alkoxy-lower alkyl is especially 2- or 3-lower alkoxy-lower alkyl, such as, for example, 2-methoxy-, 2-ethoxy-, 2-isopropoxy- or 2-butoxyethyl, 2- or 3-methoxypropyl, 2- or 3-ethoxypropyl, also 3- or 4-methoxybutyl or 3- or 4-ethoxybutyl, and halogenated lower alkyl is especially geminally, that is to say at the same carbon atom, polyhalogenated lower alkyl, such as 2,2,2-trifluoro- or 2,2,2-trichloroethyl. Phenyl-lower alkyl $R_4$ is, for example, benzyl, 2-phenylethyl, 2- or 3-phenylpropyl or 2-, 3- or 4-phenylbutyl.

Salts of the novel compounds are especially salts of compounds of the general formula I in which A represents hydroxy, that is to say $R_4$ represents hydrogen, with bases, especially pharmaceutically acceptable salts of such compounds with bases. As such salts with bases there come into consideration, for example, alkali metal or alkaline earth metal salts, such as sodium, potassium, calcium or magnesium salts, and also ammonium salts with ammonia or organic amines, such as mono- or di-lower alkylamines, for example methylamine, ethylamine, dimethylamine or diethylamine, or mono-, di- or tri(hydroxyalkyl)-amines, for example 2-aminoethanol, 2,2'-iminodiethanol or 2,2',2''-nitrilotriethanol.

As acid addition salts, especially pharmaceutically acceptable acid addition salts, of compounds of the general formula I in which $R_1$ is of basic character there come into consideration, for example, those with suitable inorganic salts, such as hydrohalic acids, for example hydrochloric acid or hydrobromic acid, and also nitric acid, sulphuric acid or phosphoric acid, or with suitable organic acids, such as carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, or organic sulphonic acids, such as lower alkanesulphonic acids optionally containing hydroxy, for example methanesulphonic acid, ethanesulphonic acid, 2-hydroxyethanesulphonic acid or ethane-1,2-disulphonic acid, or arylsulphonic acids, for example benzenesulphonic acid, 4-methylbenzenesulphonic acid or naphthalene-2-sulphonic acid, or other acidic substances, such as ascorbic acid.

The novel compounds of the general formula I and their salts exhibit valuable pharmacological properties. They have, in particular, a diuretic and naturetic action, in rats in a dosage range of from 10 to 1000 mg/kg per os and in dogs in doses upwards from 20 mg/kg per os, which may be ascertained by collecting the urine over a period of 3 hours after administration (rats) and hourly over a period of 5 hours after administration (dogs) and determining the volume of urine and of sodium, potassium and chlorine ions. In this case the excretion of potassium is increased to a lesser extent than is the excretion of sodium; the good tolerability should also be emphasised.

For example, the administration to rats of 10 mg/kg per os of 5-[(4-fluorophenyl)-acetyl]-6-methyl-2-benzodioxolecarboxylic acid or 10 mg/kg per os of 5-methyl-6-(2-thienylcarbonyl)-2-benzodioxolecarboxylic acid (3 animals per dose), in comparison with untreated control animals, increases the excretion of sodium ions by a factor of 3.6 and 2.6, respectively; of potassium ions by a factor of 2.2 and 2.4, respectively, and of chlorine ions by a factor of 2.6 and 2.3, respectively. In dogs, for example the administration of 20 mg/kg per os of 5-benzoyl-6-methyl-2-benzodioxolecarboxylic acid (3 animals per dose) increases the average excretion per minute measured during the first 3 or the first 5 hours after administration, in comparison with the average excretion per minute during the hour before administration, with regard to sodium ions by a factor of 8 and 5.5, respectively; with regard to potassium ions by a factor of only 1.2 and not at all, respectively; with regard to chlorine atoms by a factor of 9 and 6, respectively, and with regard to the volume of urine by a factor of 2.8 and 2.2, respectively. In dogs, the excretion of potassium is thus scarcely increased by this carboxylic acid.

Furthermore, the compounds of the general formula I exhibit uricosuric activity, as can be seen, for example, from experiments on Cebus apes (*Cebus apella*). In these experiments the test animals, under pentobarbital narcosis, are given, by intravenous infusion, polyfructosane in Ringer solution and the test substance in the form of an aqueous solution is injected intravenously in doses of increasing size. Urine is collected for three 10 minute periods before the first administration of test substance and then after each dose of test substance, and arterial blood is removed before the first collection period and after the last collection period. The uric acid and polyfructosane clearance is calculated from their plasma and urine concentration and finally the fractional excretion of uric acid $FE_{UR}$ is determined as a quotient of the uric acid clearance and glomerular filtration rate. In this test, compounds of the general formula I exhibit activity in a dosage range of from 1 to 10 mg/kg i.v.; for example the administration of 10 mg/kg of 5-benzoyl-6-methyl-2-benzodioxolecarboxylic acid effects almost a doubling of the fractional excretion of uric acid. Accordingly, the compounds of the general formula I and their pharmaceutically acceptable salts can be used as potassium-sparing diuretics having supplementary uricosuric action, for example for the treatment of oedema and hypertension.

The invention relates especially to compounds of the general formula I in which $R_1$ represents phenyl, thienyl or furyl, each of which is unsubstituted or substituted by lower alkyl, lower alkoxy or halogen, alk represents alkylene or alkylidene having a maximum of 3 carbon atoms, $R_2$ represents lower alkyl or halogen, $R_3$ represents hydrogen, lower alkyl or halogen, and n and A have the meanings given under formula I, but A represents especially $OR_4$ and therein $R_4$ represents hydrogen or lower alkyl, and salts of these compounds in which $R_4$ represents hydrogen with bases.

The invention relates more especially to compounds of the general formula I in which $R_1$ represents phenyl or thienyl, each of which is unsubstituted or substituted by lower alkyl, lower alkoxy or halogen, alk represents methylene, n represents 0 or 1, $R_2$ represents lower alkyl, especially methyl, or halogen, especially fluorine or chlorine, $R_3$ represents hydrogen or lower alkyl, especially methyl, and A represents $OR_4$ wherein $R_4$ represents hydrogen or lower alkyl, and the pharmaceutically acceptable salts of those compounds in which $R_4$ represents hydrogen with bases.

The invention relates most especially to compounds of the general formula I in which $R_1$ represents phenyl that is unsubstituted or substituted by lower alkyl, lower alkoxy or halogen, alk represents methylene, n represents 0 or 1, $R_2$ represents lower alkyl, especially methyl, or halogen, especially fluorine or chlorine, $R_3$ represents hydrogen or lower alkyl, especially methyl, and A represents $OR_4$ wherein $R_4$ represents hydrogen or lower alkyl, and the acyl radical is preferably bonded in the 5- or 6-position, and the pharmaceutically acceptable salts of those compounds in which $R_4$ represents hydrogen with bases.

The invention relates above all to compounds of the general formula I in which $R_1$ represents phenyl substituted by lower alkyl, especially methyl, lower alkoxy, especially methoxy, or halogen, especially fluorine, but is especially unsubstituted phenyl, alk represents methylene, n represents 1 or, especially, 0, $R_2$ represents lower alkyl, especially methyl, or halogen, especially fluorine or chlorine, $R_3$ represents hydrogen, and A represents $OR_4$ wherein $R_4$ represents hydrogen or lower alkyl, and the acyl radical is bonded in the 5- or 6-position, and the pharmaceutically acceptable salts of those compounds in which $R_4$ represents hydrogen with bases, such as the three carboxylic acids mentioned specifically above, and their pharmaceutically acceptable salts with bases.

The novel compounds of the general formula I and salts of those compounds in which A represents $OR_4$ wherein $R_4$ is hydrogen, or that have a basic character, are manufactured in a manner known per se, by (a) reacting a compound of the general formula II

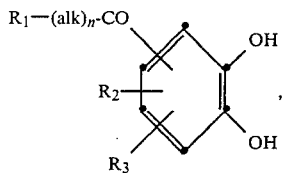
(II)

in which $R_1$, alk, n, $R_2$ and $R_3$ have the meanings given under formula I, or a salt thereof, with a compound of the general formula III

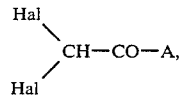
(III)

in which Hal represents halogen and A has the meaning given under formula I, or with a salt of such a compound in which A represents $OR_4$ wherein $R_4$ represents hydrogen, or (b) in a compound of the general formula IV

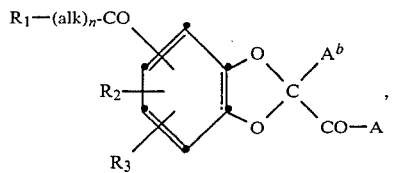
(IV)

in which $A^b$ represents carboxy, lower alkoxycarbonyl or acetyl, and $R_1$, alk, n, $R_2$, $R_3$ and A have the meanings given under formula I, replacing the radical $A^b$ by hydrogen, or (c) for the manufacture of a compound of the general formula I in which A has the meaning given under formula I with the exception of a radical $OR_4$ in which $R_4$ represents hydrogen, and $R_1$, alk, n, $R_2$ and $R_3$ have the meanings given under formula I, reacting a compound of the general formula V

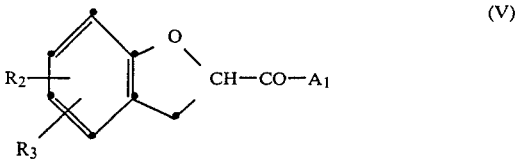
(V)

with an anhydride of a compound of the general formula VI $$R_1\text{-(alk)}_n\text{—CO—OH} \qquad (VI),$$

in which $A_1$ has the meaning given for A under formula I with the exception of a radical $OR_4$ in which $R_4$ represents hydrogen, and $R_2$ and $R_3$ and $R_1$, alk and n have the meanings given under formula I, or (d) for the manufacture of a compound of the general formula I in which A represents $OR_4$ wherein $R_4$ represents hydrogen, and $R_1$, alk, n, $R_2$ and $R_3$ have the meanings given under formula I, or a salt of this compound: in a compound of the general formula VII

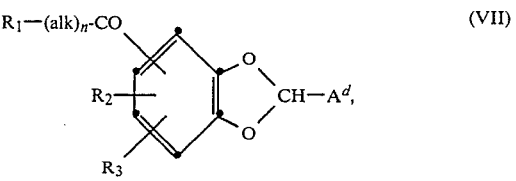
(VII)

in which $A^d$ represents a group that can be converted into the carboxy group and $R_1$, alk, n, $R_2$ and $R_3$ have the meanings given under formula I, converting the group $A^d$ into the carboxy group in free or salt form, or (e) for the manufacture of a compound of the general formula I in which A has the meaning given under formula I with the exception of a radical $OR_4$ in which $R_4$ represents hydrogen, and $R_1$, alk, n, $R_2$ and $R_3$ have the meanings given under formula I: in a compound of the general formula VIII

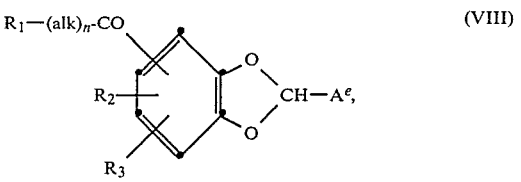
(VIII)

in which $A^e$ represents a radical that can be converted into a radical $—CO—A_1$, in which $A_1$ has the meaning given for A under formula I with the exception of a radical $OR_4$ in which $R_4$ represents hydrogen, and $R_1$, alk, n, $R_2$ and $R_3$ have the meanings given under formula I, converting the radical $A^e$ into the radical $—CO—A_1$, and, if desired, converting a resulting compound of the general formula I in a manner known per se into a different compound of the general forula I, and/or separating a compound of the general formula I obtained in the form of a racemate into the optical antipodes, and/or converting a resulting compound of the general formula I in which A represents $OR_4$ wherein $R_4$ represents hydrogen into a salt with a base or freeing such a compound from a resulting salt, or converting a resulting compound of the general formula I having basic character into an acid addition salt or freeing such a compound from a resulting salt.

In the starting materials of the general formula III, Hal is preferably chlorine or bromine, but may also be fluorine or iodine, it also being possible for two different halogen atoms to be present. The reactions according to process (a) are preferably carried out in organic solvents that are inert under the reaction conditions, for example ethereal solvents, such as, for example, dibutyl ether, 1,2-dimethoxyethane, diethyleneglycol dimethyl ether, tetrahydrofuran or dioxan; alcoholic solvents, such as, for example, methanol, ethanol, isopropanol, butanol, 2-methoxyethanol or 2-ethoxyethanol; or amide-type solvents, such as, for example, dimethylformamide or N,N,N',N',N'',N''-hexamethylphosphoric acid triamide; or in hydrocarbons, such as, for example, petroleum ether, cyclohexane, benzene or toluene. Reactions with free compounds of the general formula II and also with free haloacetic acids of the general formula III are preferably carried out in the presence of basic substances. As such basic substances there may be used, for example, organic or inorganic derivatives of alkali metals or alkaline earth metals: as organic derivatives, there may be used, for example, alkali metal or alkaline earth metal alkoxides, such as sodium or lithium methoxide, ethoxide, n-butoxide or tert.-butoxide, or barium methoxide, and as inorganic derivatives, for example, corresponding hydroxides, such as, for example, sodium, potassium or calcium hydroxide, or carbonates, such as, for example, sodium or potassium carbonate. In particular carbonates may be used in relatively large excess, for example up to 5-fold excess. When using carbonates, also other organic solvents, such as lower alkanones, for example acetone or 2-butanone, may come into consideration as being sufficiently inert.

Suitable salts of compounds of the general formula II and of dihaloacetic acids falling within the scope of the general formula III which may be used are, for example, corresponding alkali metal salts or alkaline earth metal salts. The reaction temperatures are, for example, between room temperature and approximately 150° C. and preferably between approximately 70° and 120° C.

Some of the starting materials of the general formulae II and III are known and others may be manufactured analogously to the known compounds. Thus, for example, starting materials of the general formula I may be manufactured by firstly condensing veratrole, which can be substituted in a manner corresponding to the definition for $R_2$ and $R_3$, with an acyl halide derived from a carboxylic acid of the formula $R_1$—COOH or $R_1$—alk—COOH, according to the Friedel-Crafts method, for example by means of aluminium chloride in 1,2-dichloroethane at room temperature, to form the corresponding ketone, and cleaving the two methoxy groups in this ketone in a manner known per se, for example by heating with pyridine hydrochloride or with 48% hydrobromic acid in acetic acid. If starting materials of the formula II are required in which alk represents a lower alkylidene radical, but especially a 1-lower alkylalkylidene radical, such as the 1-methylethylidene radical, it is possible, after the Friedel-Craft condensation and before the cleavage of the methoxy groups, to introduce into a keto compound in which alk represents methylene or lower alkylidene, one or preferably two lower alkyl, or one lower alkyl respectively, especially methyl, by reaction with a lower alkyl halide, such as methyl iodide, for example in a two-phase system comprising a concentrated aqueous solution of tetrabutylammonium hydroxide or bromide and an inert organic solvent, for example methylene chloride.

To carry out process (b), for example a starting material of the general formula IV in which $A^b$ represents carboxy and A, $R_1$, $R_2$ and $R_3$ have the meanings given under formula I is heated in the presence or absence of a catalyst, for example copper powder, and/or in the presence of a solvent or diluent, such as, for example, o-dichlorobenzene or 1,2,3,4-tetrahydronaphthalene, until at least an almost equimolar amount of carbon dioxide has been liberated. Starting materials of the general formula IV in which $A^b$ represents carboxy and A represents $OR_4$ wherein $R_4$ represents hydrogen are manufactured, for example, by hydrolysis of corresponding compounds in which the substituent in the corresponding position to A is $OR_4$ wherein $R_4$ represents lower alkyl, and the substituent in the corresponding position to $A^b$ is lower alkoxycarbonyl or cyano, in acidic or alkaline medium, for example by heating with a strong mineral acid in an aqueous or aqueous-organic, for example aqueous-lower alkanolic, medium, or with at least twice the molar amount of an alkali metal hydroxide, especially sodium or potassium hydroxide, for example in a lower alkanol, such as methanol, ethanol, isopropanol or n-butanol, or in a lower alkanediol or monoalkyl ether thereof, for example ethyleneglycol, 2-methoxyethanol or 2-ethoxyethanol, with water optionally being added to the above solvents in a volume ratio of water to solvent of about 1:10 to 2:1. Water may also be used as the reaction medium or, for example, a mixture of water and water-soluble, ethereal solvents, such as dioxan or tetrahydrofuran.

If the hydrolysis is effected in a water-containing mineral acid, the decarboxylation according to the process may be carried out subsequently, that is to say, in the same medium and operation.

Starting materials of the general formula IV in which $A^b$ represents carboxy and A represents a radical corresponding to the definition given under formula I with the exception of a radical $OR_4$ in which $R_4$ represents hydrogen, can be manufactured, for example, by analogous hydrolysis in alkaline medium of corresponding compounds having lower alkoxycarbonyl as the radical $A^b$ using an approximately equimolar amount of an alkali metal hydroxide instead of at least twice the molar amount. Another possibility for the manufacture of such starting materials of the general formula IV consists in the hydrogenolysis of corresponding compounds which contain benzyloxycarbonyl in the $A^b$ position.

The dealkoxycarbonylation or deacetylation of corresponding starting materials of the general formula IV, that is to say, those in which $A^b$ represents lower alkoxycarbonyl or acetyl and A represents a radical according to he definition with the exception of a radical $OR_4$ in which $R_4$ represents hydrogen, is effected, for example, by reaction with an approximately equimolar amount of an alkali metal-lower alkoxide in an anhydrous lower alkanol, and if A represents a radical $OR_4$ in which $R_4$ represents lower alkyl, it is preferable to select the same lower alkanol, for example methanol, ethanol or n-butanol, both as component of the starting ester and of the lower alkoxide and as reaction medium. It is also possible, however, to carry out a transesterification by using as reaction medium a relatively high-boiling alkanol that is not the same as the lower alkanol present as the ester component and distilling off a portion thereof simultaneously with the reaction according to the definition or to allow for only a partial transesterification if the ester of the general formula I formed as a reaction product is not to be used directly as active ingredient but is to be hydrolysed to form the corresponding acid. Instead of a lower alkanol it is also possible to use as reaction medium, for example, an inert organic solvent, such as, for example, benzene or toluene. The reaction according to the definition is carried out at room temperature or at elevated temperature, for example at the boiling temperature of the reaction medium used. If required, the resulting ester of the general formula I may, as already mentioned in connection with the transesterification, be hydrolysed to form the corresponding acid in the same operation if water is added to the reaction medium.

The starting materials of the general formula IV in which $A^b$ represents lower alkoxycarbonyl or acetyl, and the above-mentioned precursors for compounds of the general formula IV containing carboxy as radical $A^b$ that contain lower alkoxycarbonyl or cyano in the $A^b$ position, can be manufactured analogously to process (a) by reacting compounds of the general formula II with geminal dihalo compounds that differ from those of the general formula III by the presence of lower alkoxycarbonyl, acetyl or cyano in place of the hydrogen atom located adjacent to two halogen atoms, in the presence of a base.

For process (c) there are used as anhydrides of compounds of the general formula VI, for example, the halides thereof, such as chlorides or bromides, and also, for example, symmetrical anhydrides thereof. Suitable catalyst for the reaction are, for example, those for customary Friedel-Crafts condensations, such as aluminium chloride or tin(IV) chloride, and also, for example, zinc chloride, concentrated sulphuric acid, phosphoric acid, polyphosphoric acid or pyrophosphoric acid. The above-mentioned acids are preferably used when there is used as derivative of a carboxylic acid of the general formula VI a symmetrical carboxylic acid anhydride. The reaction is preferably carried out in a solvent. As such solvents there may be used, for example, halogenated hydrocarbons, such as 1,2-dichloroethane, carbon tetrachloride, methylene chloride or o-dichlorobenzene, and also, for example, aliphatic or cycloaliphatic hydrocarbons, such as heptane or cyclohexane, nitrohydrocarbons, such as nitromethane, nitrocyclohexane or nitrobenzene, and also, under mild conditions, also carbon disulphide. The reaction temperature is between approximately $-20°$ C. and $+80°$ C., preferably between approximately $0°$ and room temperature.

The starting materials of the general formula V may, for their part, be manufactured analogously to process (a) from pyrocatechol optionally substituted in a manner corresponding to the definition for $R_2$ and $R_3$, such as, for example, homopyrocatechol (4-methylpyrocatechol) with dihaloacetic acids or functional derivatives thereof corresponding to the general formula III. Some of the functional derivatives of compounds of the general formula VI required as second reactant are known and others may be manufactured analogously to the known derivatives.

In the manufacture of compounds of the general formula I in which A represents the radical $OR_4$ wherein $R_4$ represents hydrogen, according to process (d) the conversion of a group $A^d$ into the carboxy group can be effected in a manner known per se, especially by hydrolysis in an alkaline or acidic medium, it being possible in the former case to obtain a salt also directly. Starting materials for the hydrolysis are in the first instance those compounds of the general formula I in which A is not a radical $OR_4$ in which $R_4$ represents hydrogen, especially those compounds which can readily be hydrolysed, such as, for example, the lower alkyl esters, but also other functional derivatives of the carboxylic acids desired as end products, such as, for example, nitriles and imido esters, especially imido-lower alkyl esters, of carboxylic acids falling within the scope of the general formula I. The hydrolysis is effected, for example, in lower alkanolic or aqueous-lower alkanolic alkali hydroxide solutions from room temperature to approximately $100°$ C. or the boiling temperature of the reaction medium. Lower alkyl esters, such as methyl or ethyl esters, and other readily cleavable esters of the carboxylic acids falling within the scope of the general formula I can be hydrolysed under even milder conditions, for example in the presence of potassium or sodium carbonate at room temperature or, if necessary, at a slightly elevated temperature, for example $40°$ C., in an aqueous-organic medium, for example by adding water to the reaction mixture obtained in the reaction according to (a) in a water-miscible solvent, such as, for example, 1,2-dimethoxyethane. From the alkali metal salt solutions of the carboxylic acids falling within the scope of the general formula I, which solutions are obtained first of all, it is possible either to obtain the corresponding pure alkali salt directly by concentration and filtration or total evaporation of the solvent and recrystallisation, or to free the carboxylic acid first of all and then to purify it, for example by recrystallisation and, if desired, convert it into a salt again with a suitable inorganic or organic base. Functional derivatives of the carboxylic acids falling with the scope of the general formula I may also be converted into the free carboxylic acid of the general formula I in an acidic medium, for example by heating in sulphuric acid diluted with water, for example 60–70% sulphuric acid, or in lower alkanolic-aqueous hydrochloric acid.

The required functional derivatives of carboxylic acids that fall within the scope of the general formula I are manufactured, for example, according to process (a), (b) or (c), and other functional derivatives, such as, for example, nitriles, are manufactured analogously to these processes.

Starting materials of the general formula VIII are, according to the nature of the radical $A^e$ they contain, for example, carboxylic acids, carboxylic acid halides or anhydrides, especially mixed anhydrides, and also activated esters, for example cyanomethyl esters, and also lower alkyl esters, which can be reacted, optionally in the presence of condensation agents, with hydroxy compounds of the general formula IX

$$R_4-OH \qquad (IX)$$

or ammonia or amines of the general formula X

$$HN\begin{array}{c}R_5\\ \\R_6\end{array} \qquad (X)$$

in whieh formulae $R_4$, $R_5$ and $R_6$ have the meanings given under formula I, or salts, especially alkali metal or alkaline earth metal salts, of free carboxylic acids, which can be reacted with reactive esters of hydroxy compounds of the general formula IX, such as halides, or organic sulphonic acid esters, for example lower alkanesulphonic or arenesulphonic acid esters, such as methanesulphonic or p-toluenesulphonic acid esters, or alternatively with carbamic acid halides, especially chlorides, derived from amines of the general formula X in which the radicals $R_5$ and $R_6$ are other than hydrogen; and also, for example, the imido esters, especially imido-lower alkyl esters, or nitriles, that can be hydrolysed to form esters, especially lower alkyl esters, and to form unsubstituted amides, respectively. Free carboxylic acids can be reacted, for example, also with diazo-lower alkanes to form lower alkyl esters, or with isocyanates that are derived from primary amines falling within the scope of the general formula X, to form N-mono-substituted amides.

The reactions of free carboxylic acids with hydroxy compounds of the general formula IX are effected advantageously in the presence of an acidic water-removing catalyst, such as a protonic acid, for example in the presence of hydrochloric or hydrobromic acid, sulphuric acid, phosphoric acid or boric acid, benzenesulphonic or toluenesulphonic acid, or a Lewis acid, for example boron trifluoride etherate, in an excess of the hydroxy compound used and/or in an inert solvent, for example in a hydrocarbon of the benzene series, such as benzene or toluene, a halogenated hydrocarbon, such as chloroform, methylene chloride or chlorobenzene, or in an ethereal solvent, such as tetrahydrofuran, if necessary with removal by distillation, for example azeotropic, of the water freed in the reaction. It is also possible to carry out the reactions in the presence of other water-binding condensation agents, for example in the presence of carbodiimides substituted by hydrocarbon radicals, such as N,N'-diethyl-, N,N'-dicyclohexyl- or N-ethyl-N'-(3-dimethylaminopropyl)-carbodiimide, in inert organic solvents, for example those mentioned above. Halides and mixed anhydrides are reacted, for example, in the presence of acid-binding agents, for example organic, especially tertiary, nitrogen bases, such as, for example, triethylamine, ethyl diisopropylamine or pyridine, or alternatively inorganic bases, for example, alkali metal or alkaline earth metal hydroxides or carbonates, such as sodium, potassium or calcium hydroxide or carbonate, in inert organic solvents, for example those mentioned above, and, if necessary, while heating. The reactions of reactive esters of carboxylic acids of the general formula I, for example the cyanomethyl esters, with hydroxy compounds of the general formula IX are carried out, for example, in a solvent that is inert towards the reactants, for example in a hydrocarbon, such as toluene or xylene, an ethereal solvent, such as tetrahydrofuran or dioxan, or alternatively, at moderate temperatures, in an ester, such as ethyl acetate, in a temperature range of from approximately 0° to approximately 120° C., preferably from room temperature to approximately 60° C. For the transesterification of lower alkyl esters of carboxylic acids of the general formula I. it is preferable to use hydroxy compounds of the general formula IX having a boiling point clearly above that of the esterified lower alkanol and to carry out the reaction, for example, in an excess of the hydroxy compound and/or in an inert organic solvent that preferably also has a boiling point clearly higher than that of the lower alkanol, preferably in the presence of a catalyst, for example an alkali metal-lower alkoxide, such as sodium or potassium methoxide or ethoxide, at elevated temperature and, preferably, while distilling off the lower alkanol that is liberated. The hydrolysis of imido esters, especially of imido-lower alkyl esters, of carboxylic acids of the general formula I is effected, for example, by means of a water-containing mineral acid, such as hydrochloric or sulphuric acid; and imido ester hydrochlorides obtained, for example, by the addition of hydrogen chloride to nitriles and reaction with anhydrous hydroxy compounds of the general formula IX, especially lower alkanols, can, after the addition of water, be hydrolysed directly to the corresponding esters, or, for example, the corresponding ester of the general formula I can also be obtained from a mixture of nitrile, hydroxy compound and sulphuric acid having a suitable water content, without isolating the imido ester formed in situ.

The reaction of free carboxylic acids of the general formula I with compounds of the general formula X is effected, for example, in the presence of the above-mentioned water-binding agents and in the above-mentioned inert organic solvents, but it is also possible to convert the ammonium salts formed first of all from the free carboxylic acids and the compounds of the general formula X into amides of the general formula I by heating, optionally in a suitable organic solvent having a medium or high boiling point, such as, for example, xylene, chlorobenzene or 1,2,3,4-tetrahydronaphthalene, and removal by distillation, optionally azeotropic, of the water liberated in the reaction.

As reactive functional derivatives of carboxylic acids of the general formula I for the reaction with compounds of the general formula X and as associated condensation agents and solvents there come into consideration substantially the same derivatives, condensation agents and solvents as those indicated above for reactions with hydroxy compounds of the general formula IX, except that as acid-binding agents and optionally as the only reaction medium, it is possible to use instead of other bases, i.e. tertiary organic bases, alternatively an excess of the compound of the general formula X to be reacted. The partial hydrolysis of the corresponding nitriles, mentioned above as a further possibility for forming N-unsubstituted amides, may be carried out, for example, by means of water-containing mineral acids, such as hydrochloric acid or dilute sulphuric acid, at room temperature or at moderately elevated temperature.

The free carboxylic acids of the general formula I required as starting materials for process (e) can be manufactured according to processes (a), (b), (c) and/or (d), and the reactive functional derivatives thereof can be manufactured, for example, from the free carboxylic acids, in a manner known per se.

Resulting salt-forming compounds of the formula I can be converted into salts in a manner known per se; for example, those with hydroxy as radical A may be converted with corresponding bases, such as, for example, alkali metal hydroxides, into salts with bases, or those having a basic character may be converted into their acid addition salts. Preferably pharmaceutically acceptable salts are manufactured.

Resulting salts can be converted into the free compounds in a manner known per se, for example by treatment with an acidic reagent, such as a mineral acid, or with a base, for example an alkali metal hydroxide solution, such as sodium hydroxide solution.

The compounds, and their salts, can also be obtained in the form of their hydrates, or their crystals may include the solvent used for crystallisation.

As a result of the close relationship between the novel compounds of the general formula I in which A represents hydroxy in free form and in the form of their salts with bases, and between those compounds in which the radical $R_1$ has basic character in free form and in the form of acid addition salts, hereinbefore and hereinafter the free compounds and their salts shall be understood to mean optionally also the corresponding salts and free compounds, respectively, where appropriate with regard to meaning and purpose.

Depending upon the number of centres of asymmetry and upon the starting materials and procedures chosen, the novel compounds may be obtained in the form of racemates or mixtures of racemates (mixtures of diastereoisomers) or, where desired, also in the form of pure antipodes.

Resulting mixtures of racemates may be separated into the pure racemates or diastereoisomers in known manner, on the basis of the physicochemical differences between the constituents, for example by chromatography and/or fractional distillation. Resulting racemates may also be separated into the optical antipodes according to known methods, for example by recrystallisation from an optically active solvent, with the aid of microorganisms or by reaction of an acidic end product of the general formula I with an optically active base that forms salts with the racemic acid, or by reaction of a basic end product of the general formula I with an optically active acid, and separating the salts obtained in this manner, for example on the basis of differing solubility, into the diastereoisomers, from which the antipodes may be freed by the action of suitable agents. Advantageously the more active of the two antipodes is isolated.

The invention relates also to those embodiments of the process according to which a compound obtainable as an intermediate at any stage of the process is used as starting material and the remaining process steps are carried out, or a starting material is used in the form of a salt and/or racemate or antipode, or, especially, is formed under the reaction conditions.

The starting materials used in the processes of the present invention are preferably those which result in the compounds described at the beginning as being especially valuable. The present invention relates also to novel starting materials and to processes for their manufacture.

The invention relates also to pharmaceutical compositions that contain compounds of the general formula I as active ingredients, and to processes for their manufacture.

The pharmaceutical compositions according to the invention are for enteral, such as oral or rectal, and for parenteral administration to warm-blooded animals. The dosage of the active ingredient, which may be administered alone or together with a customary carrier or adjunct, depends upon the species of warm-blooded animal, age and individual condition and upon the method of administration. The daily doses are between 0.5 and 30 mg/kg for mammals, the daily dose for a mammal weighing approximately 70 kg preferably being between 25 and 900 mg, especially between 50 and 600 mg, depending on individual condition and age. Appropriate oral dosage unit forms, for example dragées, tablets or capsules, contain preferably from 12.5 to 300 mg, especially from 25 to 200 mg, of an active ingredient according to the invention, that is to say, a compound of the general formula I or a pharmaceutically acceptable salt of a compound of the general formula I that is capable of salt formation, together with pharmaceutical carriers.

The pharmaceutical compositions of the present invention are manufactured in a manner known per se, for example by means of conventional mixing, granulating, confectioning, dissolving or lyophilising processes. For example, pharmaceutical compositions for oral use can be obtained by combining the active ingredient with solid carriers, optionally granulating a resulting mixture and processing the mixture or granulate, if desired or necessary after the addition of suitable adjuncts, to form tablets or dragée cores.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, maize, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical dose units for oral administration are dry-filled capsules consisting of gelatine and also soft sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical compositions there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances which increase the viscosity, for example sodium carboxymethylcellulose, sorbitol and/or dextran, and, optionally, also stabilisers.

The invention relates also to the use of the novel compounds of the formula I and the pharmaceutically acceptable salts thereof as pharmacologically active compounds, especially as diuretics having supplementary uricosuric action, preferably in the form of pharmaceutical compositions in a method for the prophylactic and/or therapeutic treatment of the human or animal body, especially for the treatment of oedema and/or hypertension.

The following Examples illustrate the invention described above but are not intended to limit its scope in any way. Temperatures are given in degrees Centigrade.

EXAMPLE 1

While stirring at 5° to 10°, 33.3 g (0.25 mol) of aluminium chloride are added in portions over a period of 30 minutes to a solution of 20.8 g (0.1 mol) of 5-methyl-2-benzodioxolecarboxylic acid ethyl ester and 16.9 g (0.12 mol) of benzoyl chloride in 250 ml of 1,2-dichloroethane and the mixture is stirred for a further 30 minutes at 5° to 10° and then heated to room temperature. It is then poured onto a mixture of approximately 500 g of ice and approximately 1000 ml of water. There is first formed an emulsion from which the organic phase gradually separates out. This is separated off and washed in succession twice with 100 ml of water each time, once with 200 ml of 2N sodium carbonate solution and twice with 100 ml of water. The combined aqueous phases are in turn extracted twice with 100 ml of chloroform each time and the residue from these extracts is combined with the organic phase. The latter is then dried with sodium sulphate, filtered and concentrated by evaporation. The crude 5-benzoyl-6-methyl-2-benzodioxolecarboxylic acid ethyl ester that remains is purified by column chromatography on 1000 g of silica gel using chloroform/petroleum ether/ethyl acetate in the ratio 10:10:1 as solvent and eluant. After first-run fractions of approximately 7 to 10% of the total amount, the above-mentioned ester is obtained as a main product of viscous consistency which can be further used directly.

14.2 g (0.05 mol) of 5-benzoyl-6-methyl-2-benzodioxolecarboxylic acid ethyl ester are dissolved in 160 ml of ethanol, 120 ml of 2N sodium hydroxide solution are added and the mixture is stirred at room temperature for 30 minutes. The ethanol is then evaporated off under reduced pressure, a small quantity of fuller's earth is added to the alkaline solution that remains and the whole is filtered with suction. 150 ml of 2N hydrochloric acid are added to the filtrate and the acid that separates out is extracted with approximately 800 ml of ethyl acetate and then twice more with 100 ml of ethyl acetate each time. The organic phases are combined, washed twice with 100 ml of water each time, dried with sodium sulphate, filtered and concentrated by evaporation. The residue is dissolved in a small quantity of ether and petroleum ether is added to the solution until it becomes turbid. An impurity separates out which, after the addition of a small quantity of fuller's earth, is filtered off. The clear yellow filtrate is concentrated by evaporation, dissolved in 25 ml of ethyl acetate and again filtered. Cyclohexane is added to the filtrate until it becomes turbid and the filtrate is inoculated with the desired acid, if available, yielding 5-benzoyl-6-methyl-2-benzodioxolecarboxylic acid having a melting point of 119°–122°. Further reaction product can be obtained from the residue of the mother liquors by dissolving in ethyl acetate and adding cyclohexane as above.

The 4-methyl-2-benzodioxolecarboxylic acid ethyl ester used as starting material is manufactured as follows:

(a) 124 g (1 mol) of homopyrocatechol (4-methylpyrocatechol) are introduced at approximately 15° over a period of 10 minutes into a sodium ethoxide solution, prepared in customary manner by dissolving 46.0 g (2 mol) of sodium in 1500 ml of absolute ethanol under dry, oxygen-free nitrogen and with the exclusion of water, and a dark solution that is blue at the surface is formed. 157 g (1 mol) of dichloroacetic acid ethyl ester are then added dropwise at approximately 10° over a period of 20 minutes. The reaction mixture is then stirred at room temperature for one hour and then boiled under reflux for 6 hours. 10 g of "silica gel H according to Stahl" are added, while stirring, to the resulting dark-brown solution and the whole is filtered through diatomaceous earth. The dark-brown filtrate is concentrated by evaporation in vacuo and the black, viscous residue is dissolved in sufficient ether and 300 ml of 5% sodium bicarbonate solution; the ether phase is first extracted with sodium bicarbonate solution and then, in order to remove any homopyrocatechol still present, extracted 6 times with 50 ml of 2N sodium hydroxide solution each time, and finally is washed twice with water, dried over sodium sulphate, filtered and concentrated by evaporation in a rotary evaporator. The red liquid that remains is distilled in vacuo, the desired 5-methyl-2-benzodioxolecarboxylic acid ethyl ester passing over under 26 mbar at 155° to 158°.

The 5-methyl-2-benzodioxolecarboxylic acid ethyl ester can also be manufactured from homopyrocatechol in two stages as follows:

(b) While stirring under a nitrogen atmosphere, 186.2 g (1.5 mol) of homopyrocatechol and 236.3 g (184.3 ml, 1.5 mol) of dichloroacetic acid ethyl ester are dissolved, in succession, in 1000 ml of 1,2-dimethoxyethane and then 1040.2 g (7.54 mol) of pulverised potassium carbonate are added in portions, the temperature rising to over 50° and a thick suspension being produced. This reaction mixture is heated under reflux (bath temperature), while stirring, for 5 hours, then cooled to 40° and approximately 2000 ml of water are added slowly. A brown emulsion is formed which also contains solid substance. The 1,2-dimethoxyethane is distilled off in a rotary evaporator, fuller's earth is added to the black solution that remains and the whole is filtered through diatomaceous earth. The dark-brown filtrate is adjusted to pH 2 with concentrated hydrochloric acid and, foaming vigorously, the crude acid precipitates out in the form of a resin. The mixture is extracted three times with ethyl acetate, the combined ethyl acetate solutions are washed twice with water, dried over sodium sulphate and concentrated by evaporation—to leave light-brown, resin-coated crystals. These crystals are dissolved in approximately 700 ml of ethyl acetate and the black solution is mixed with 1400 ml of saturated sodium bicarbonate solution and, foaming gently, an emulsion is formed from which the aqueous phase separates out again. This phase is extracted twice with 300 ml of ethyl acetate each time and the ethyl acetate solutions are in turn extracted twice with 500 ml of water each time. The aqueous phases are combined with that obtained above, adjusted to pH 1 to 2 with approximately 130 ml of concentrated hydrochloric acid and extracted three times with ether. The ether solutions are each washed twice with water, then combined and dried over sodium sulphate; fuller's earth is added and the whole is filtered and concentrated by evaporation. In order to remove any resin still present, the resulting brown oil is extracted with 200 ml of warm cyclohexane and then 6 times with 100 ml of warm cyclohexane each time, the portions being decanted off in each case. On cooling the combined portions there is obtained 5-methyl-2-benzodioxolecarboxylic acid in the form of white crystals having a melting point of 108°–110°.

(c) 104.1 g (0.5 mol) of 5-methyl-2-benzodioxolecarboxylic acid are boiled under reflux for 15 minutes in 1000 ml of absolute ethanol that contains 0.5 ml of concentrated hydrochloric acid. The clear yellow solution is then concentrated by evaporation and the residue is dissolved in a mixture of ether and 1N sodium bicarbonate solution. The ether phase is extracted twice with water and the combined aqueous phases are in turn extracted twice with ether. The combined ether phases are dried over sodium sulphate, filtered and concentrated by evaporation, the crude 5-methyl-2-benzodioxolecarboxylic acid ethyl ester remaining behind in the form of a brown oil. During subsequent distillation in vacuo it passes over under approximately 21 mbar at 152° to 154°. Instead of the white substance having a melting point of 108°–110°, it is also possible to use as starting material the resin-coated crystals obtained under (b).

EXAMPLE 2

While stirring at 5° to 10°, 46.6 g (0.35 mol) of aluminium chloride are added in portions over a period of 25 minutes to a solution of 31.2 g (0.15 mol) of 5-methyl-2-benzodioxolecarboxylic acid ethyl ester and 28.5 g (21.3 ml, 0.18 mol) of 2-fluorobenzoyl chloride in 350 ml of 1,2-dichloroethane. The reaction mixture is then stirred for a further 90 minutes at 5°–10° and for 30 minutes at room temperature after which all the aluminium chloride has dissolved. After standing at room temperature for approximately 24 hours, the reaction mixture is poured onto approximately 2 kg of a mixture of ice and water. The organic phase is separated off, washed once with 2N hydrochloric water, twice with water, once with 1N sodium bicarbonate solution and twice more with water, then dried over sodium sulphate and concentrated by evaporation in vacuo. The crude 5-(2-fluorobenzoyl)-6-methyl-2-benzodioxolecarboxylic acid ethyl ester obtained as residue can be further processed directly.

59 g (0.15 mol) of 5-(2-fluorobenzoyl)-6-methyl-2-benzodioxolecarboxylic acid ethyl ester are dissolved in 270 ml of ethanol and, at room temperature, 130 ml of 2N sodium hydroxide solution are added, the solution turning a dark colour and becoming slightly heated. After allowing to stand at room temperature for 2 hours, the ethanol is distilled off in vacuo, there is added to the residue approximately half its volume of water and the whole is extracted twice with ether. The aqueous solution is then acidified with approximately 50 ml of 6N hydrochloric acid and the acid that separates out is extracted with ethyl acetate. The organic phase is washed twice with water, dried and concentrated by evaporation and the crude 5-(2-fluorobenzoyl)-6-methyl-2-benzodioxolecarboxylic acid remains in the form of a sand-coloured powder. For purification, it is dissolved in a small quantity of ethyl acetate, an equal volume of cyclohexane is added and then fuller's earth is added to the hot solution and the whole is filtered through diatomaceous earth. The filtrate is concentrated in a rotary evaporator, left to stand at room temperature and finally cooled to approximately 10°. The crystals are filtered off, recrystallised with a small quantity of ethyl acetate/cyclohexane and then recrystallised again from ethyl acetate/cyclohexane. The substance obtained in this manner melts at 152°–156°.

EXAMPLE 3

In a manner analogous to that described in Example 2, there is obtained, using 28.5 g (0.18 mol) of 4-fluorobenzoyl chloride, 5-(4-fluorobenzoyl)-6-methyl-2-benzodioxolecarboxylic acid ethyl ester in the form of an oily crude product, and from 16.5 g (0.05 mol) of the aforementioned product there is obtained 5-(4-fluorobenzoyl)-6-methyl-2-benzodioxolecarboxylic acid having a melting point of 93°–94° (from ethyl acetate).

EXAMPLE 4

In a manner analogous to that described in Example 2 there is obtained, using 34.1 g (0.02 mol) of 4-methoxybenzoyl chloride, 5-(4-methoxybenzoyl)-6-methyl-2-benzodioxolecarboxylic acid ethyl ester, and from 17.1 g (0.05 mol) of the above product there is obtained 5-(4-methoxybenzoyl)-6-methyl-2-benzodioxolecarboxylic acid having a melting point of 55°–57° (from ethyl acetate/petroleum ether).

EXAMPLE 5

In a manner analogous to that described in Example 2 there is obtained, using 31.2 g (0.18 mol) of (4-fluorophenyl)-acetyl chloride, 5-[(4-fluorophenyl)-acetyl]-6-methyl-2-benzodioxolecarboxylic acid in the form of an oily crude product, and from 17.2 g (0.05 mol) of the above product there is obtained 5-[(4-fluorophenyl)-acetyl]-6-methyl-2-benzodioxolecarboxylic acid having a melting point of 106°–109° (from ethyl acetate/cyclohexane).

EXAMPLE 6

While stirring at 5° to 8°, 33.3 g (0.25 mol) of aluminium chloride are added in portions over a period of 30 minutes to a solution of 20.8 g (0.1 mol) of 5-methyl-2-benzodioxolecarboxylic acid ethyl ester and 17.7 g (0.12 mol) of 2-thiophenecarbonyl chloride in 250 ml of 1,2-dichlorethane. After stirring for a further 30 minutes at 5° to 8°, the cooling bath is removed and the reaction mixture is stirred for a further 3 hours at room temperature. A further 100 ml of 1,2-dichlorethane are added and the reaction mixture is poured onto a mixture of 500 g of ice and 1000 ml of water. The organic phase is separated off and washed in succession twice with 100 ml of water each time, once with 200 ml of 2N sodium carbonate solution and twice more with 100 ml of water each time. The aqueous phase, on the other hand, is extracted twice with 100 ml of chloroform each time and the residue from these extracts is combined with the organic phase. The latter is then dried with sodium sulphate, filtered and concentrated by evaporation in vacuo. The residue is chromatographed over a column of 1000 g of silica gel using chloroform/petroleum ether/ethyl acetate in a ratio of 10:10:1 as solvent and eluant. After approximately 10% of the total quantity of first-run products, the desired 5-methyl-5-[(2-thienyl)-carbonyl]-2-benzodioxolecarboxylic acid ethyl ester is eluted as a main product of approximately 80%. The appropriate fractions crystallise spontaneously and can be used directly for the next stage. A small quantity of petroleum ether and ethyl acetate is added to a sample and the resulting crystal suspension is filtered. The crystals of the above ester obtained in this manner melt at 69°–70°.

15.9 g (0.05 mol) of 5-methyl-6-[(2-thienyl)-carbonyl]-2-benzodioxolecarboxylic acid ethyl ester are dissolved in 160 ml of ethanol while heating to approximately 60° and 75 ml of 2N sodium hydroxide solution are added, while stirring, to the solution which has been cooled again to room temperature. After stirring for 15 minutes at approximately 20°, the ethanol is evaporated off in vacuo, a small quantity of fuller's earth is added to the solution that remains and the whole is filtered and 90 ml of 2N hydrochloric acid are added thereto. The acid that separates out is extracted with approximately 300 ml of ethyl acetate, the ethyl acetate solution is washed twice with 150 ml of water each time and the aqueous phases are again extracted with ethyl acetate. The combined organic phases are dried with sodium sulphate, filtered and concentrated and the desired product crystallises. The product is filtered off and recrystallised from ethyl acetate. The 5-methyl-6-[(2-thienyl)-carbonyl]-2-benzodioxolecarboxylic acid obtained in this manner melts at 136°–137°.

EXAMPLE 7

A mixture of 4.05 g (0.015 mol) of 1-(4,5-dihydroxy-2-methylphenyl)-2-methyl-2-phenyl-1-propanone, 2.83 g (0.018 mol) of dichloroacetic acid ethyl ester and 5.6 g (0.04 mol) of anhydrous potassium carbonate is stirred in 15 ml of dimethylformamide at 90° under a nitrogen atmosphere for 2 hours. As much of the dimethylformamide as possible is then evaporated off in a rotary evaporator. The residue is dissolved in 100 ml of water and the solution is left to stand at room temperature for 1 hour. It is then rendered acidic to Congo Red with dilute hydrochloric acid, and the 5-methyl-6-(2-methyl-2-phenylpropionyl)-2-benzodioxolecarboxylic acid that is liberated is extracted with ethyl acetate and the resulting solution is concentrated by evaporation. Recrystallisation of the residue yields the pure carboxylic acid in the form of small colourless needles having a melting point of 117°–119°.

The dihydroxyketone required is manufactured as follows:

(a) While stirring, 80.0 g (0.6 mol) of aluminium chloride are added in portions to a solution of 84.1 g (0.5 mol) of 1,2-dimethoxy-4-methylbenzene (homopyrocatechol dimethyl ether or 4-methylveratrole) in 750 ml of 1,2-dichloroethane, the temperature being maintained at a maximum of 20° by cooling in an ice bath. Then, at 15°–20°, 85.0 g (approximately 73 ml, 0.55 mol) of phenylacetyl chloride are added dropwise over a period of one hour, a moderate evolution of hydrogen chloride occurring and the aluminium chloride being dissolved.

The reaction mixture is then stirred at room temperature for a further 6 hours and then poured onto 3000 ml of a mixture of ice and water. The resulting layers are separated and the organic phase is washed in succession with 2N hydrochloric acid, twice with water, then with 1N sodium bicarbonate solution and twice more with water, dried, filtered and concentrated by evaporation. The partly crystallised residue is caused to crystallise completely from ether/petroleum ether (boiling range 40°–65°) yielding the 1-(4,5-dimethoxy-2-methylphenyl)-2-phenyl-1-ethanone having a melting point of 45°–48°.

(b) While stirring at room temperature, a solution of 13.5 g (0.05 mol) of 1-(4,5-dimethoxy-2-methylphenyl)-2-phenyl-1-ethanone and 21.3 g (9.35 ml, 0.15 mol) of methyl iodide in 135 ml of methylene chloride is added dropwise over a period of 45 minutes to 100 ml of a 40% solution of tetrabutylammonium hydroxide (approximately 0.15 mol). A moderately exothermic reaction heats the reaction mixture to approximately 35°. The reaction mixture is then stirred for a further 10 hours without heating or cooling. The phases are then separated and the organic phase is washed twice with water, dried over sodium sulphate, filtered and concentrated by evaporation. 300 ml of ether are added to the residue and the tetrabutylammonium iodide crystallises out. This is filtered off and the filtered material is washed with ether. The filtrate is concentrated by evaporation and the above residue is dissolved in a mixture of petroleum ether (boiling range 40°–60°), chloroform and ethyl acetate 10:10:1 and adsorbed on 450 g of silica gel. Elution with the afore-mentioned mixture and concentration of the first 4 liters of eluate by evaporation yields 1-(4,5-dimethoxy-2-methylphenyl)-2-methyl-2-phenyl-1-propanone in the form of an oil which can be further used directly.

(c) 8.0 g of the oily product of (b) (approximately 0.026 mol) are mixed with 50 g of pyridine hydrochloride and the mixture is heated at 200° (internal temperature) for 4 hours. The reaction mixture is then allowed to cool, ice and 50 ml of 2N hydrochloric acid are added and the reaction product that separates out is extracted with ethyl acetate. Concentrating the resulting solution by evaporation and recrystallising the partly crystallised residue from ethyl acetate/cyclohexane yields 1-(4,5-dihydroxy-2-methylphenyl)-2-methyl-2-phenyl-1-propanone having a melting point of 189°–191°.

EXAMPLE 8

A solution of 71.0 g (0.24 mol) of 5-benzoyl-6-methyl-2-benzodioxolecarboxylic acid (melting point 120°–122°, cf. Example 1), in 200 ml of acetonitrile and a solution of 41.2 g (0.25 mol) of D-ephedrine (base) in 300 ml of acetonitrile, each at approximately 30°, are combined and cooled in an ice bath and the crystals that are deposited are filtered off. The resulting crystal fraction is recrystallised four times from acetonitrile, yielding the D-ephedrine salt of (+)-5-benzoyl-6-methyl-2-benzodioxolecarboxylic acid in the form of colourless, fine needles having a melting point of 149°–150° (sinters from 145°).

Dissolving in water, acidifying with 2N hydrochloric acid and filtering off yields the corresponding free acid which, after crystallisation from 50 ml of ethyl acetate with the addition of 20 ml of petroleum ether, (boiling range 40°–60°), melts at 145°–147°; $[\alpha]_D^{20} + 67°$ (c=1% in acetone).

The carboxylic acid is freed and separated off from the mother liquor residues of the above crystallisation operations and reacted in analogous manner in the form of a solution in acetonitrile with the corresponding solution of L-ephedrine. The salt of L-ephedrine with the (−)-5-benzoyl-6-methyl-2-benzodioxolecarboxylic acid, obtained as a crude product, is, also in analogous manner, first recrystallised four times from acetonitrile and then the carboxylic acid is freed from the resulting pure salt which has a melting point of 149°–150° (sinters from 145°). The melting point of the carboxylic acid, after recrystallisation from ethyl acetate/petroleum ether (see above), is 145°–147°, $[\alpha]_D^{20} -67° \pm 1°$ (c=1% in acetone).

EXAMPLE 9

A suspension of 46.7 g (0.338 mol) of freshly calcined potassium carbonate in 180 ml of 1,2-dimethoxyethane is stirred for 10 minutes under nitrogen in a high-speed agitator. Then, while stirring normally, 15.7 g (67.6 mmol) of (4,5-dihydroxy-2-fluorophenyl)-phenylmethanone and 10.6 g (67.6 mmol) of dichloroacetic acid ethyl ester are added and the mixture is heated to 70°. After 6 hours, an additional 3.9 g (20 mmol) of dichloroacetic acid ethyl ester are added and the mixture is boiled for a further 15 hours. Water is then added and the whole is adjusted to pH 1–2 with hydrochloric acid, partially concentrated by evaporation in vacuo and extracted with ethyl acetate. The organic phases are washed with water and saturated sodium chloride solution, dried over sodium sulphate and concentrated completely by evaporation. The residue is esterified with ethanol/p-toluenesulphonic acid. The ester is purified by chromatography on silica gel using an ethyl acetate/n-hexane mixture (ratio 1:1) as eluant. After concentrating the appropriate fractions by evaporation, the ester is dissolved in methanol and hydrolysed with 1N sodium hydroxide solution at room temperature. Ice/water is added to the reaction mixture and the whole is acidified and extracted with ethyl acetate. The combined ethyl acetate extracts are washed, dried and concentrated by evaporation. The yellow residue is boiled up with n-hexane and filtered with suction. After recrystallising the filtered material twice from 1,2-dichloroethane, the 5-benzoyl-6-fluoro-2-benzodioxolecarboxylic acid is obtained in the form of white crystals having a melting point of 152°–153.5°.

The (4,5-dihydroxy-2-fluorophenyl)-phenylmethanone required can be manufactured as follows:

(a) Six bomb tubes, each containing 4.8 g (30.0 mmol) of 4-fluoro-1,2-dimethoxybenzene (obtained from 3,4-dimethoxyaniline by a Balz-Schiemann reaction), 7.5 g (37.5 mmol) of (2-pyridinyl)-benzoate and 300 ml of trifluoroacetic acid, are heated at 100° for 4½ hours while stirring magnetically. The contents of all six bomb tubes is poured into 600 ml of water while stirring vigorously and the solid substance that separates out is filtered with suction. The filtrate is extracted several times with toluene. The solid substance is dissolved in the combined toluene extracts. The toluene solution is washed with water and saturated sodium chloride solution, dried over magnesium sulphate and concentrated to dryness by evaporation. The resulting semi-solid oil is dissolved in 500 ml of warm isopropanol and treated with carbon. The filtered solution is concentrated in vacuo until crystallisation begins. After complete crystallisation, the (4,5-dimethoxy-2-fluorophenyl)-phenylmethanone is filtered with suction and washed with cold isopropanol, yielding white crystals having a melting point of 102°–104°.

The same substance can also be manufactured as follows:

(b) 12.7 g (95 mmol) of aluminium trichloride in 80 ml of 1,2-dichloroethane are stirred under nitrogen and cooled to 3°. 13.35 g (95 mmol) of benzoyl chloride are added. At 30°, this red solution is added dropwise over a period of 25 minutes to a solution of 12.55 g (80.3 mmol) of 1,2-dimethoxy-4-fluorobenzene (4-fluoroveratrole) in 80 ml of 1,2-dichloroethane. The reaction mixture is stirred for a further 3 hours at 3°, then for 3½ hours at room temperature and then poured onto a mixture of 250 ml of ice and 20 ml of concentrated hydrochloric acid. The organic phase is separated off and the aqueous phase is extracted several times with ether. Organic phase and ether solutions are combined, washed with 1N sodium hydroxide solution, water and with saturated sodium chloride solution, dried over magnesium sulphate and concentrated by evaporation. The resulting yellow oil is stirred with 50 ml of ether in an ice bath until crystallisation takes place, yielding the desired (4,5-dimethoxy-2-fluorophenyl)-phenylmethanone in the form of white crystals having a melting point of 102°–103°.

For demethylation, a mixture of 21.0 g (80.7 mmol) of (4,5-dimethoxy-2-fluorophenyl)-phenylmethanone, 80 ml of glacial acetic acid and 80 ml of hydrobromic acid (48%) is boiled under reflux for 17 hours. The reaction mixture is then poured onto ice/water and extracted several times with ethyl acetate. The combined extracts are washed with water and saturated sodium chloride solution, treated with activated carbon, dried over sodium sulphate and concentrated to dryness by evaporation. The residue is recrystallized twice from 1,2-dichloroethane yielding the (4,5-dihydroxy-2-fluorophenyl)-phenylmethanone having a melting point of 169.5°–171°.

EXAMPLE 10

A suspension of 83 g (0.60 mol) of freshly calcined potassium carbonate in 250 ml of 1,2-dimethoxyethane is stirred for 10 minutes under nitrogen with a high-speed agitator. Then, while stirring normally, 28.10 g (0.113 mol) of (4,5-dihydroxy-2-chlorophenyl)-phenylmethanone and 19.5 g (0.124 mol) of dichloroacetic acid ethyl ester are added. The reaction mixture is boiled under reflux for 20 hours, then 400 ml of water are added and the whole is stirred for a further 1 hour. A portion of the solvent is evaporated off in vacuo and the aqueous phase is extracted several times with ethyl acetate. The organic extracts are combined, washed with water and saturated sodium chloride solution, treated with activated carbon, dried over magnesium sulphate and concentrated by evaporation. The resulting brown oil is chromatographed on silica gel using the eluant chloroform/methanol/concentrated ammonia 22:7:1. The fractions containing the uniform substance are combined, partially concentrated by evaporation, acidified with 1N hydrochloric acid and extracted with ethyl acetate. The organic phases are washed, dried and concentrated by evaporation as mentioned above. The resulting yellow oil is triturated with hot hexane until crystallisation takes place. The crystals are filtered off and triturated a second time with hot hexane. There is thus obtained the desired 5-benzoyl-6-chloro-2-benzodioxolecarboxylic acid in the form of a white powder having a melting point of 146°–148°.

The (4,5-dihydroxy-2-chlorophenyl)-phenylmethanone required as starting material can be manufactured by two methods:

(a) A mixture of 300 ml of carbon disulphide, 80 g (0.60 mol) of powdered aluminium trichloride and 28.9 g (0.20 mol) of 2-chloro-1,2-benzenediol is stirred for 15 minutes at room temperature and then for 1 hour at 40°. 30.9 g (0.220 mol) of benzoyl chloride are then added over a period of 10 minutes and the whole is stirred for a further 15 minutes at 40° and heated in order slowly to distil off the carbon disulphide. The dry residue is then heated to 140° (bath temperature) in the course of 1 hour and maintained at this temperature for 3½ hours. The brown solid mass is cooled, 300 ml of 3N hydrochloric acid and 200 ml of ethyl acetate are added and the mixture is stirred until completely dissolved. The organic phase is separated off and the aqueous phase is extracted with ethyl acetate. The combined organic phases are washed with water and saturated sodium chloride solution, dried over sodium sulphate, treated with carbon and concentrated by evaporation. The dark-brown residue is dissolved in 100 ml of 1,2-dichloroethane, 105 ml of n-hexane are added and the whole is triturated until crystallisation takes place. The crystals are filtered with suction and recrystallised from dichloroethane/hexane. The (2-chloro-4,5-dihydroxyphenyl)-phenylmethanone, obtained in the form of white crystals (melting point 130°–135°), can be further reacted directly.

(b) The afore-mentioned dihydroxyketone can also be obtained in two stages analogously to Example 9a) and b). The (2-chloro-4,5-dimethoxyphenyl)-phenylmethanone required for this purpose can be obtained by acylating 4-chloro-1,2-dimethoxybenzene with benzoyl chloride in the presence of iodine. It is easier to obtain, however, if one equivalent of 4-chloro-1,2-dimethoxybenzene is heated in a bomb tube at 150° for 2 hours with 1.1 equivalents of (2-pyridinyl)-benzoate in trifluoroacetic acid. After working up and demethylation in a manner analogous to Example 9b), the desired (4,5-dihydroxy-2-chlorophenyl)-phenylmethanone is obtained.

EXAMPLE 11

Tablets containing 100 mg of 5-benzoyl-6-methyl-2-benzodioxolecarboxylic acid can be manufactured, for example, having the following composition:

| Composition | per tablet |
| --- | --- |
| 5-benzoyl-6-methyl-2-benzo-dioxolecarboxylic acid | 100 mg |
| lactose | 50 mg |
| wheat starch | 73 mg |
| colloidal silica | 13 mg |
| talc | 12 mg |
| magnesium stearate | 2 mg |
| | 250 mg |

Manufacture

The active ingredient is mixed with lactose, a portion of the wheat starch and with colloidal silica and the mixture is forced through a sieve. A further portion of the wheat starch is made into a paste with 5 times the quantity of water on a water bath and the powder mixture is kneaded with this paste until a slightly plastic mass is formed. The mass is forced through a sieve of approximatly 3 mm mesh width and dried and the dry granulate is again forced through a sieve. The remainder of the wheat starch, the talc and the magnesium stearate are then admixed. The resulting mixture is pressed into 250 mg tablets having (a) breaking notch(es).

EXAMPLE 12

For the manufacture of 1000 capsules, each containing 100 mg of active ingredient, 100 g of 5-benzoyl-6-methyl-2-benzodioxolecarboxylic acid are mixed with 173.0 g of lactose, and the mixture is moistened evenly with an aqueous solution of 2.0 g of gelatine and granulated through a suitable sieve (for example sieve III according to Ph. Helv. V.). The granulate is mixed with 10.0 g of dried maize starch and 15.0 g of talc, and 1000 size 1 hard gelatine capsules are filled with equal quantities of this mixture.

Instead of 5-benzoyl-6-methyl-2-benzodioxolecarboxylic acid it is also possible to use in the above Examples a different compound of the general formula I or a pharmaceutically acceptable salt of a compound of the general formula I that is capable of salt formation, for example one of the compounds described in Examples 2 to 8, or a pharmaceutically acceptable salt of such a compound.

EXAMPLE 13

46.6 g (0.35 mol) of aluminum chloride are added portionwise within 25 minutes at 5° to 10° C., with stirring, to a solution of 31.2 g (0.15 mol) of 5-methyl-1,3-benzodioxole-2-carboxylic acid ethyl ester and 54.7 g (0.18 mol) of 4-(dipropylsulfamoyl)-benzoyl chloride in 350 ml of 1,2-dichloroethane. The reaction mixture is then stirred for a further 90 minutes at 5°–10° C. and for 30 minutes at room temperature, after which time all the aluminum chloride has been dissolved. After standing for about 24 hours at room temperature, the reaction mixture is poured into about 2 kg of an ice/water mixture. The organic phase is separated; it is subsequently washed once with 2N hydrochloric acid, twice with water, once with 1N sodium bicarbonate solution and again twice with water; it is afterwards dried over sodium sulfate and concentrated by evaporation in vacuo. The 5-[4-(dipropylsulfamoyl)-benzoyl]-6-methyl-1,3-benzodioxole-2-carboxylic acid ethyl ester obtained as residue melts at 97°–99° C. after recrystallisation.

EXAMPLE 14

There is obtained in a manner analogous to that of Example 1, with the use of 42 g of 2-chlorobenzoyl chloride, the 5-(2-chlorobenzoyl)-6-methyl-1,3-benzodioxole-2-carboxylic acid ethyl ester as an oily product, which is directly further processed.

34 g (0.1 mol) of the above ethyl ester are dissolved in 180 ml of ethanol, and at room temperature are added 87 ml of 2N sodium hydroxide solution, in the course of which a deepening in colour and slight heating occur. The mixture is left standing at room temperature for 2 hours, and the ethanol is then distilled off in vacuo; to the residue is added about half its volume of water, and extraction is performed twice with ether. The aqueous solution is thereupon acidified with about 35 ml of 6N hydrochloric acid, and the precipitated acid is extracted with ethyl acetate. The organic phase is washed twice with water, dried, and concentrated by evaporation to thus leave the crude 5-(2-chlorobenzoyl)-6-methyl-1,3-benzodioxole-2-carboxylic acid as a sand-coloured powder. To purify this, it is dissolved in a small amount of ethyl acetate, and the same volume of cyclohexane is added; to the hot solution is then added bleaching earth, and the whole is filtered through diatomaceous earth. The filtrate is concentrated in a rotary evaporator; it is subsequently left to stand at room temperature, and finally cooled to about 10° C. The crystals are filtered off, washed with a small amount of ethyl acetate/cyclohexane, and again recrystallised from ethyl acetate/cyclohexane. The substance thus obtained melts at 133°–135° C.

EXAMPLE 15

A mixture of 25.9 g (0.084 mol) of (2-bromophenyl)-(3,4-dihydroxy-6-methylphenyl)-methanone, 68 g of potassium carbonate (anhydrous) and 21.3 g (0.0975 mol) of dibromoacetic acid is stirred in 150 ml of dimethyl formamide for 5 hours at 80° C. under nitrogen protection. The dimethyl formamide is then distilled off to the maximum possible extent in a rotary evaporator. The residue is dissolved in 300 ml of water, and in the cold state the solution is made acid to a Congo-red indicator with dilute hydrochloric acid. The precipitating crude acid is extracted with ethyl acetate, and subsequently 5-(2-bromobenzoyl)-6-methyl-1,3-benzodioxole-2-carboxylic acid recrystallised from toluene; m.p. 123°–125° C.

The starting ketone is produced in the following manner:

(a) A solution of 20 g of bisphosphorus pentoxide in 200 ml of methanesulfonic acid is poured over 20.7 g (0.1 mol) of 2-bromobenzoic acid and 15.2 g (0.1 mol) of 1,2-dimethoxy-4-methylbenzene, and the mixture is heated, with stirring, for 30 minutes at 70° C. The mixture is then poured into ice-water and extracted with ether. After concentration by evaporation, the ether extracts yield (2-bromophenyl)-(3,4-dimethoxy-6-methylphenyl)-methanone as a brown product of honey-like consistency.

(b) 38.8 g of 4-(2-bromobenzoyl)-5-methyl-1,2-dimethoxybenzene and 80 g of pyridine hydrochloride are heated, while being stirred with a magnetic stirrer, at 180°–200° C. for 2 hours. After the resulting melt has cooled, 1000 ml of 1N hydrochloric acid are added and extraction is performed with ether. The ether extracts are dried, and concentrated by evaporation to thus yield, after crystallisation from toluene, (2-bromophenyl)-(3,4-dihydroxy-6-methylphenyl)-methanone in the form of colourless crystals, m.p. 177°–178° C.

EXAMPLE 16

By a procedure analogous to that described in Example 3, there is obtained, with the use of 13.0 g (0.0435 mol) of 4-(2,6-dichlorobenzoyl)-5-methyl-1,2-benzenediol and 11.0 g (0.504 mol) of dibromoacetic acid, 5-(2,6-dichlorobenzoyl)-6-methyl-1,3-benzodioxole-2-carboxylic acid as colourless crystals, m.p. 118°–122° C.

The starting ketone is produced as follows.

(a) Reaction of 9.5 g (0.05 mol) of 2,6-dichlorobenzoic acid and 7.5 g (0.05 mol) of 1,2-dimethoxy-4-methylbenzene, in a manner analogous to that of Example 3(a), yields (2,6-dichlorophenyl)-(3,4-dimethoxy-6-methyl-phenyl)-methanone as colourless crystals, m.p. 101°–103° C.

(b) In a manner analogous to that of Example 3(b), there is obtained from the product of (a), by ether cleavage, (2,6-dichlorophenyl)-(3,4-dihydroxy-6-methylphenyl)-methanone as sand-coloured crystals, m.p. 206°–207° C.

EXAMPLE 17

By a method analogous to that in Example 3, there is obtained, by reaction of 23.8 g (0.0925 mol) of (3,4-dihydroxy-6-methylphenyl)-(2,6-dimethylphenyl)-methanone with 23.4 g (0.107 mol) of dibromoacetic acid: 5-(2,6-dimethylbenzoyl)-6-methyl-1,3-benzodioxole-2-carboxylic acid as colourless crystals, m.p. 129°–131° C. (from toluene).

The starting ketone is produced as follows.

(a) In a manner analogous to that of Example 3(a), there is obtained, by the use of 2,6-dimethylbenzoic acid and 1,2-dimethoxy-4-methylbenzene: (3,4-dimethoxy-6-methylphenyl)-(2,6-dimethylphenyl)-methanone as sand-coloured crystals, m.p. 95°–97° C.

(b) By a procedure analogous to that of Example 3(b), there is obtained, by ether cleavage of 28 g (0.098 mol) of the product of (a): (3,4-dihydroxy-6-methylphenyl)-(2,6-dimethylphenyl)-methanone as colourless crystals, m.p. 193°–195° C. (from toluene).

EXAMPLE 18

By reaction of 20.5 g (0.084 mol) of 4-(2-methylbenzoyl)-5-methyl-1,2-benzenediol and 21.3 g (0.0977 mol) of dibromoacetic acid, analogously to Example 3, and subsequent salt formation with 2-amino-2,2-bis-(hydroxymethyl)-ethanol, there is obtained the [1,1-bis-(hydroxymethyl)-2-hydroxyethyl]-ammonium salt of 5-(2-methylbenzoyl)-6-methyl-1,3-benzodioxole-2-carboxylic acid as colourless crystals, m.p. 160°–162° C.

The starting ketone is produced as follows.

(a) By the reaction of 13.6 g (0.1 mol) of 2-methylbenzoic acid with 15.2 g (0.1 mol) of 1,2-dimethoxy-4-methylbenzene, analogously to Example 3(a), there is obtained (3,4-dimethoxy-6-methylphenyl)-(2-methylphenyl)-methanone as a brown resin-like product.

(b) By ether cleavage of the product of (a), analogously to Example 3(b), there is obtained (3,4-dihydroxy-6-methylphenyl)-(2-methylphenyl)-methanone as sand-coloured crystals, m.p. 149°–150° C.

EXAMPLE 19

By reaction of 17.3 g (0.075 mol) of (3,4-dihydroxy-6-methylphenyl)-(3-pyridyl)-methanone with 16.5 g (0.075 mol) of dibromoacetic acid, analogously to Example 3, there is obtained 5-methyl-6-nicotinoyl-1,3-benzodioxole-2-carboxylic acid as sand-coloured crystals, m.p. 250°–232° C. (from dimethyl sulfoxide/water).

The starting ketone is produced as follows.

250 ml of thionyl chloride are poured over 61.5 g (0.5 mol) of nicotinic acid, and the mixture is refluxed for 2 hours. The thionyl chloride is subsequently distilled off under normal pressure, and 500 ml of carbon disulfide are added to the residue. There are then added within 15 minutes, with vigorous stirring, 250 g of aluminum chloride, and the mixture is stirred for 2 hours at room temperature. In the course of 30 minutes are then added portionwise 62 g (0.5 mol) of 4-methyl-1,2-benzenediol. The thick suspension is stirred until no further hydrogen chloride escapes; the carbon disulfide is subsequently distilled off at a bath temperature of 90° C. under normal pressure; the residue is put at the same temperature for one hour under a vacuum of about 14 mbar; normal pressure is afterwards established with nitrogen, and the reaction mixture is heated at 100° C. for a further 8 hours.

The mixture is cooled for further processing; the hard foam-like substance is comminuted and poured into water. The reaction product is extracted by means of ethyl acetate, and the ethyl acetate solution is concentrated by evaporation to thus yield (3,4-dihydroxy-6-methyl)-(3-pyridyl)-methanone in the form of sand-coloured crystals, m.p. 220°–223° C.

EXAMPLE 20

By reaction of 26.3 g (0.885 mol) of (2-bromo-4,5-dihydroxyphenyl)-phenylmethanone and 38.6 g (0.177 mol) of dibromoacetic acid, analogously to Example 3, and subsequent salt formation with sodium hydroxide solution, there is obtained the sodium salt of 5-benzoyl-6-bromo-1,3-benzodioxole-2-carboxylic acid as colourless crystals, which melt above 150° C. with decomposition.

The starting ketone is produced as follows.

(a) By reaction of benzoic acid with 1-bromo-3,4-dimethoxybenzene, in a manner analogous to that of Example 3(a), there is obtained (2-bromo-4,5-dimethoxyphenyl)-phenylmethanone, m.p. 71°–72° C.

(b) There is obtained analogously to Example 3(b) from the product of (a), by ether cleavage, (2-bromo-4,5-dihydroxyphenyl)-phenylmethanone as brown oil.

EXAMPLE 21

In order to produce 1000 capsules each containing 100 mg of active substance, 100 g of 5-(2-chlorobenzoyl)-6-methyl-1,3-benzodioxole-2-carboxylic acid are mixed with 173.0 g of lactose; the mixture is then uniformly moistened with an aqueous solution of 2.0 g of gelatine, and is granulated through a suitable sieve (for example sieve III according to Ph. Helv. V.). The granulate is mixed with 10.0 g of dried maize starch and 15.0 g of talcum, and the mixture is evenly filled into 1000 hard gelatine calsules, size 1.

Any other of the compounds described in the preceding Examples can be used as active substance in place of the above compound.

What is claimed is:

1. A benzodiozole derivative of the formula I

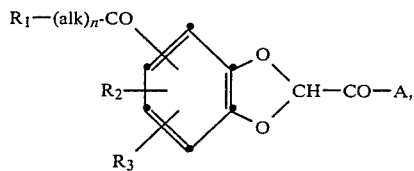

in which
$R_1$ represents phenyl, thienyl, pyridyl or furyl, each of which is unsubstituted or substituted by lower alkyl, lower alkoxy, halogen, or dilower alkyl sulfamoyl, alk represents an alkylene or alkylidene radical having a maximum of 5 carbon atoms, n represents 0 or 1, $R_2$ and $R_3$ each represents, independently of the other, hydrogen, lower alkyl, lower alkoxy or halogen, and A represents the radical O-$R_4$, wherein $R_4$ represents hydrogen or lower alkyl, or A represents the radical

in which either $R_5$ and $R_6$ represents, independently of the other, hydrogen or lower alkyl, or $R_5$ and $R_6$ are bonded to one another and, together with the adjacent nitrogen atom, represent unsubstituted or lower alkyl-substituted tetra- to hexamethyleneimino or 4-morpholinyl, in the form of racemates or optical antipodes, an the salts of a compound of the formula I in which A represents OR$_4$ wherein R$_4$ represents hydrogen, with bases, and the acid addition salts of a compound of the formula I in which the radical $R_1$ has a basic character.

2. The compound of claim 1 which is 5-(4-(dipropylsulfamoyl)-benzoyl)-6-methyl-1,3-benzodioxol-2-carboxylic acid ethyl ester.

3. The compound of claim 1 which is 5-methyl-6-nicotinoyl-1,3-benzodioxole-2-carboxylic acid.

4. A pharmaceutical composition having diuretic activity comprising a therapeutically effective amount of a compound according to claim 1 or of a pharmaceutically acceptable salt of a compound according to claim 1 that is capable of salt formation, together with at least one pharmaceutical carrier.

5. A method for treating oedema or hypertension in a mammal comprising administering to said mammal a therapeutically effective amount of a compound according to claim 1 or of a pharmaceutically acceptable salt of a compound according to claim 1 that is capable of salt formation.

* * * * *